United States Patent [19]

Carlson et al.

[11] Patent Number: 5,586,027
[45] Date of Patent: Dec. 17, 1996

[54] METHOD AND APPARATUS FOR DETERMINING FLOW RATES IN MULTI-PHASE FLUID FLOW MIXTURES

[75] Inventors: Norman R. Carlson; Mohammad J. Davarzani, both of Houston, Tex.

[73] Assignee: Western Atlas International, Inc., Houston, Tex.

[21] Appl. No.: 557,377

[22] Filed: Nov. 13, 1995

Related U.S. Application Data

[63] Continuation of Ser. No. 384,603, Feb. 3, 1995, abandoned, which is a continuation of Ser. No. 213,457, Mar. 14, 1994, abandoned, which is a continuation of Ser. No. 90,480, Jul. 12, 1993, abandoned, which is a continuation of Ser. No. 963,000, Oct. 19, 1992, abandoned, which is a continuation of Ser. No. 697,538, Apr. 30, 1991, abandoned, which is a continuation of Ser. No. 364,889, Jun. 12, 1989, abandoned.

[51] Int. Cl.⁶ .............................. G06F 19/00; E21B 47/00
[52] U.S. Cl. ............................................................ 364/422
[58] Field of Search ..................... 364/422, 509, 364/510; 73/3, 155, 861.04

[56] References Cited

U.S. PATENT DOCUMENTS

| | | | |
|---|---|---|---|
| 3,954,006 | 5/1976 | Anderson et al. | 73/155 |
| 4,441,361 | 4/1984 | Carlson et al. | 73/155 |
| 4,441,362 | 4/1984 | Carlson | 73/155 |
| 4,576,042 | 3/1986 | Johnson | 73/155 |
| 4,800,752 | 1/1989 | Piers | 73/155 |
| 4,836,017 | 6/1989 | Bozek | 73/155 |
| 4,928,758 | 5/1990 | Siegfried | 73/155 X |
| 5,051,922 | 9/1991 | Toral et al. | 364/510 |
| 5,052,220 | 10/1991 | Piers | 73/155 |
| 5,095,758 | 3/1992 | Cox et al. | 73/861.04 |
| 5,099,697 | 3/1992 | Agar | 73/861.04 |

*Primary Examiner*—Donald E. McElheny, Jr.
*Attorney, Agent, or Firm*—Darryl M. Springs

[57] ABSTRACT

Method and apparatus are disclosed for determining the water cut of an oil-water flow in a wellbore having a known deviation angle less than 90. A first step includes generating a set of predicted response curves where each response curve relates discrete selected values of the water cut to test values representative of a value of the flow mixture functionally related to measured responses of a selected logging instrument capable of distinguishing between the water and oil phases of the flow mixture for a selected oil-water total flow rate and at a borehole deviation within a selected range of deviation values that include the known borehole deviation. Then the selected logging instrument combination is introduced into the borehole for measuring the total flow rate of the oil-water mixture and the values representative of the responses of the selected logging instrument distinguishing between the oil and water phases of the oil-water mixture. A value functionally related to the measured value representative of the responses of the selected logging instrument is generated. From the set of predicted response curves an estimated value of the water cut of the oil-water mixture at the measured borehole total flow rate of the oil-water mixture is determined in response to the generated value functionally related to the measured value representative of the responses of the selected logging tool.

4 Claims, 6 Drawing Sheets

METHOD AND APPARATUS FOR DETERMINING FLOW RATES IN MULTI-PHASE FLUID FLOW MIXTURES

This is a continuation of application Ser. No. 08/384,603, filed Feb. 3, 1995 (now abandoned), which is a continuation of application Ser. No. 08/213,457 filed on Mar. 14, 1994 (now abandoned), which is a continuation of application Ser. No. 08/090,480 filed on Jul. 12, 1993 (now abandoned), which is a continuation of application Ser. No. 07/963,000 filed Oct. 19, 1992 (now abandoned), which is a continuation of application Ser. No. 07/697,538 filed on Apr. 30, 1991 (now abandoned), which is a continuation of application Ser. No. 07/364,889 filed on Jun. 12, 1989 (now abandoned).

BACKGROUND OF THE INVENTION

This invention relates generally to methods and apparatus for determining flow rates of fluid in a pipe or well, and more specifically, to methods and apparatus for determining the flow rates of individual single phases of the total flow rate of a multi-phase fluid flow mixture in a wellbore.

In producing wells it is common to find the well fluid consisting of multiple phases, such as oil and water, oil and gas, or oil, water and gas. Often, one or more of such phases is an undesirable part of the well production. For example, in the case of a flow regime comprising oil and water, as is common in such producing wells, the oil is the fluid phase desired to be produced while the water phase is typically an undesirable portion in the production flow. In a well which produces oil and water phases, logging surveys often are made for the purpose of establishing the flow profile. This profile indicates the rates at which oil and water are produced from each formation interval of interest. A profile is desired which accurately indicates those intervals producing oil, those producing water, and those producing both fluids. Such a profile is indispensable for improving the oil production, reducing the water phase production, and characterizing and managing the reservoir.

For flow profiling, it is necessary to establish, at a desired depth, the total flow rate of the oil and water phases, as well as the water cut, which is the water flow rate expressed as a fraction of the total flow rate. The logging instruments used in the survey typically produce responses from which the total flow rate and the water holdup can be derived. Water holdup is defined as the volumetric concentration of water in the well bore. In order to generate the flow profile, it is necessary to relate the water cut to the water holdup and the total flow rate at any depth of the well.

In customary practice, water cut is derived from a relationship which involves the water holdup, the total flow rate, and the slip velocity, which is the amount by which the flow velocity of the oil phase exceeds the velocity of the water phase due to the difference between the fluids' densities. There are a number of difficulties attendant to this method of deriving the water cut:

1. Since slip velocity cannot be measured in the well survey, it must be estimated independently;
2. Charts for estimating the slip velocity usually pertain to bubble flow, i.e., oil bubbles percolating through water. These charts should not be used in the many instances when the flow regime cannot be characterized as bubble flow; and
3. Available charts and correlations for slip velocity pertain to vertical bubble flow, and should not be relied upon when the oil-water flow is in a deviated well bore.

Accordingly, the present invention presents a new method and apparatus of relating the water cut to the total flow rate and the water holdup. The method is applicable in both vertical and deviated well bores, and it is not limited to a bubble flow regime. The method is based on a set of predicted response curves for fluid density and fluid capacitance instruments in oil-water flows. These curves are derived from measurements recorded in a test flow loop prior to determining the flow rates of the oil-water regime in the borehole.

SUMMARY OF THE INVENTION

In accordance with one principle of the invention, method and apparatus are disclosed for determining the flow rate of a selected single phase of a multi-phase flow mixture expressed as fraction of the total flow rate of the flow mixture in a wellbore having a known deviation angle less than 90°, and includes a first step of generating a set of predicted response curves wherein each such response curve relates discrete selected values of the flow rate of the selected single phase of the multi-phase flow mixture expressed as a fraction of the total flow rate Of the flow mixture to test values representative of the volumetric concentration of the selected single phase of the multi-phase flow mixture functionally related to measured responses of a selected logging instrument capable of distinguishing between the phases of the flow mixture for a selected fluid mixture total flow rate and at a borehole deviation within a selected range of deviation values that include the known borehole deviation. Then the selected logging instrument combination is introduced into the borehole for measuring the total flow rate of the fluid mixture including the selected single phase thereof, measuring values representative of the responses of the selected logging instrument distinguishing between the phases of the multi-phase flow mixture generating a value representative of the volumetric concentration of the selected single phase of the multi-phase flow mixture functionally related to the measured value representative of the responses of the selected logging instrument. Finally, the invention includes determining from the set of predicted response curves an estimated value of the flow rate of the selected singlephase of the multi-phase flow mixture expressed as a fraction of the total flow rate of the flow mixture at the measured borehole total flow rate in response to the generated value representative of the volumetric concentration of the selected single phase of the flow mixture.

The total flow of the selected single phase of the multi-phase fluid flow regime is determined as a product of the total flow of the multi-phase fluid and the flow rate of the selected single phase of the fluid flow. If the multi-phase fluid flow consists of two-phases, then the remaining phase may be determined by subtracting the selected single phase flow from the total fluid flow.

In accordance with a further principle of this invention, method and apparatus are disclosed for determining the water cut of an oil-water flow in a wellbore having a known deviation angle less than 90°, and includes a first step of generating a set of predicted response curves wherein each such response curve relates discrete selected values of the water cut to test values representative of the volumetric concentration of the water phase of the flow mixture functionally related to measured responses of a selected logging instrument capable of distinguishing between the water and oil phases of the flow mixture for a selected oil-water total flow rate and at a borehole deviation within a selected range of deviation values that include the known borehole deviation. Thereafter, the selected logging instrument combination is introduced into the borehole for measuring the total flow rate of the oil-water mixture, then measuring values representative of the responses of the selected logging instrument distinguishing between the oil and water phases of the oil-water mixture, generating a value functionally related to the measured value representative of the responses of the selected logging instrument, and then determining from the set of predicted response curves an estimated value of the water cut of the oil-water mixture at the measured borehole total flow rate of the oil-water mixture in response to the generated value functionally related to the measured value representative of the responses of the selected logging tool.

The water flow is determined as a product of the measured total fluid flow and the flow rate of water. The total flow of the oil phase of the total fluid flow may then be determined by subtracting the water flow from the measured total oil-water flow.

Accordingly, one primary feature of the present invention is to provide a new and improved method and apparatus for determining the flow rate of each phase of a multi-phase fluid flow mixture.

It is yet another feature of the present invention to provide a new and improved method and apparatus for determining the volumetric fraction of the components present in the multiphase flow regime.

Still another feature of the present invention is to provide a new and improved method and apparatus for accurately determining the volumetric fractions of the components present in a multi-phase flow regime over a range of borehole deviations less than 90°.

BRIEF DESCRIPTION OF THE DRAWINGS

In order that the manner in which the above-recited advantages and features of the invention are attained can be understood in detail, a more particular description of the invention may be had by reference to specific embodiments thereof which are illustrated in the accompanying drawings, which drawings form a part of this specification.

In the drawings.

DETAILED DESCRIPTION OF THE PREFERRED EMBODIMENTS

Figure 1:
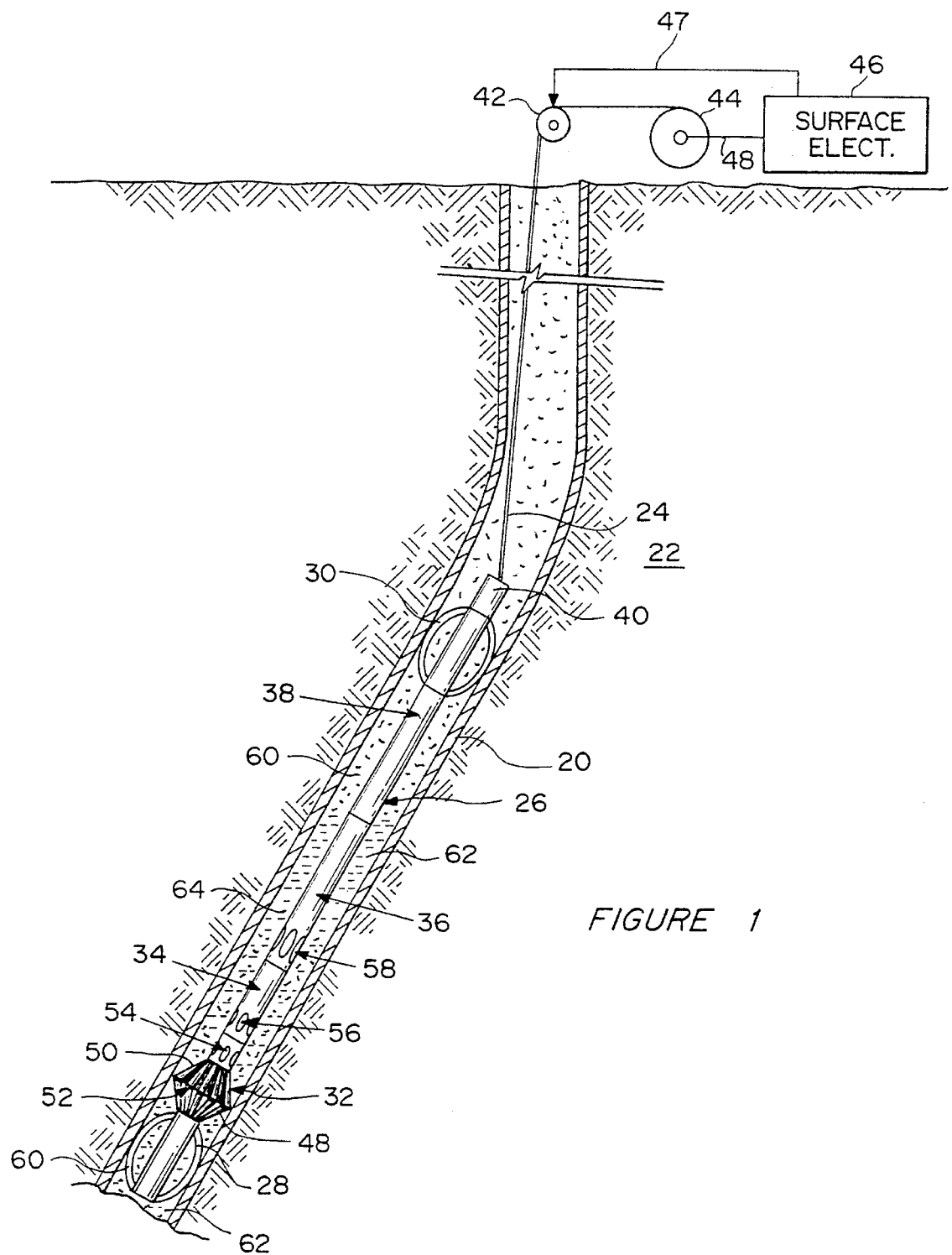
FIG. 1 is a side elevational view, partly in cross-section, of a selection logging instrument combination disposed in a borehole for measuring fluid density and capacitance and measuring the multi-phase fluid total flow.

Referring now to the drawings, and particularly to FIG. 1, a deviated cased borehole 20 penetrating an earth formation 22 is shown in cross-section. Although the borehole shown in FIG. 1 is illustrated as having set casing, the present invention may also be utilized in an uncased borehole. Disposed within borehole 20, and suspended from the wireline cable 24, is a selected logging instrument combination 26, for measuring the fluid density and capacitance and the total flow rates in a multi-phase flow regime in accordance with the present invention. The instrument combination 26 is positioned in the center of the borehole by centralizer sections 28 and 30. Disposed up stream of the centralizer 28 is a diverting flow ("basket") flowmeter 32, a fluid density logging instrument 34, a fluid capacitance logging instrument 36, and an instrumentation/telemetry tool section 38 interconnected to the upstream centralizer 30. An attachment sub 40 is interconnected upstream of centralizer 30 and interconnects to the wireline cable 24 supporting the instrument string downhole. Wireline 24 also provides a conduit for telemetry and command signals exchanged between the downhole electronics instrument 38 and the surface electronics system 46.

At the earth's surface is shown a cable sheave 42 that supports the tool 26 by wireline 24 and directs the cable to a drum 44. Surface electronics module 46 is connected to the downhole tool and cable 24 via an electrical interconnection 48. Information relative to depth of the instrument 26 is obtained from measuring the depth of the instrument via measuring the cable passing over sheave 42 (means not shown) and which depth information is provided to the module 46 through cable 47.

The diverting ("basket") flowmeter 32 has a plurality of spring straps 50 longitudinally disposed on the tool with the upper ends thereof carrying "leaved" overlapping sections 48. When the instrument package 26 is traversing the borehole the spring straps 50 are flat to facilitate movement of the tool in the borehole. When the tool has reached a predetermined logging depth, the spring straps 50 are actuated to centrally "bow" out into contact with the borehole wall. The leaved sections 48 are spread to form a "funnel"— the outer edges of which contact the borehole wall and divert substantially all of the fluid flow in the wellbore through the openings 52 through a restricted passage in which is axially disposed a measurement spinner (not shown). The rotational motion of the spinner due to the fluid flow through the flowmeter is calibrated to measure flow in a direct relationship to the number of rotations of the flowmeter spinner.

The multi-phase fluid flow regime in the borehole may be separated into differing strata due to differences in specific gravity and the deviation angle of the borehole as shown in FIG. 1 with the heavier water phase 62 appearing on the low side of the borehole 20 while the lighter oil phase 60 appears at the high side of the borehole 20. The diverting flowmeter 32 forces the multi-phase fluids at higher velocity to mix while traversing the flowmeter, and the mixed fluid regime will be discharged from the flowmeter 32 through discharge ports 54. Unless the multi-phase fluid regime is composed of phases having great differences in specific gravity (such as gas and oil) the mixed fluid (such as water and as herein described) will tend to remain mixed for a short time in the borehole as shown at 64 before again separating into distinct phases 60 (oil) and water (62) uphole as shown.

The fluid flow, after discharge from ports 54 in the flowmeter, enter the ports 56 in the conventional gamma ray fluid density logging instrument 34. The fluid density instrument 34 measures the density of the fluid oil-water mixture, ρm. The fluid flow then enters the ports 58 in the conventional fluid capacitance instrument 36 for measuring the dielectric property of the wellbore fluid which is expressed as a frequency response, fm, for the fluid oil-water mixture. The data acquisition instrument 38 permits simultaneous recording of flowmeter, fluid density and fluid capacitance responses.

Figure 2:
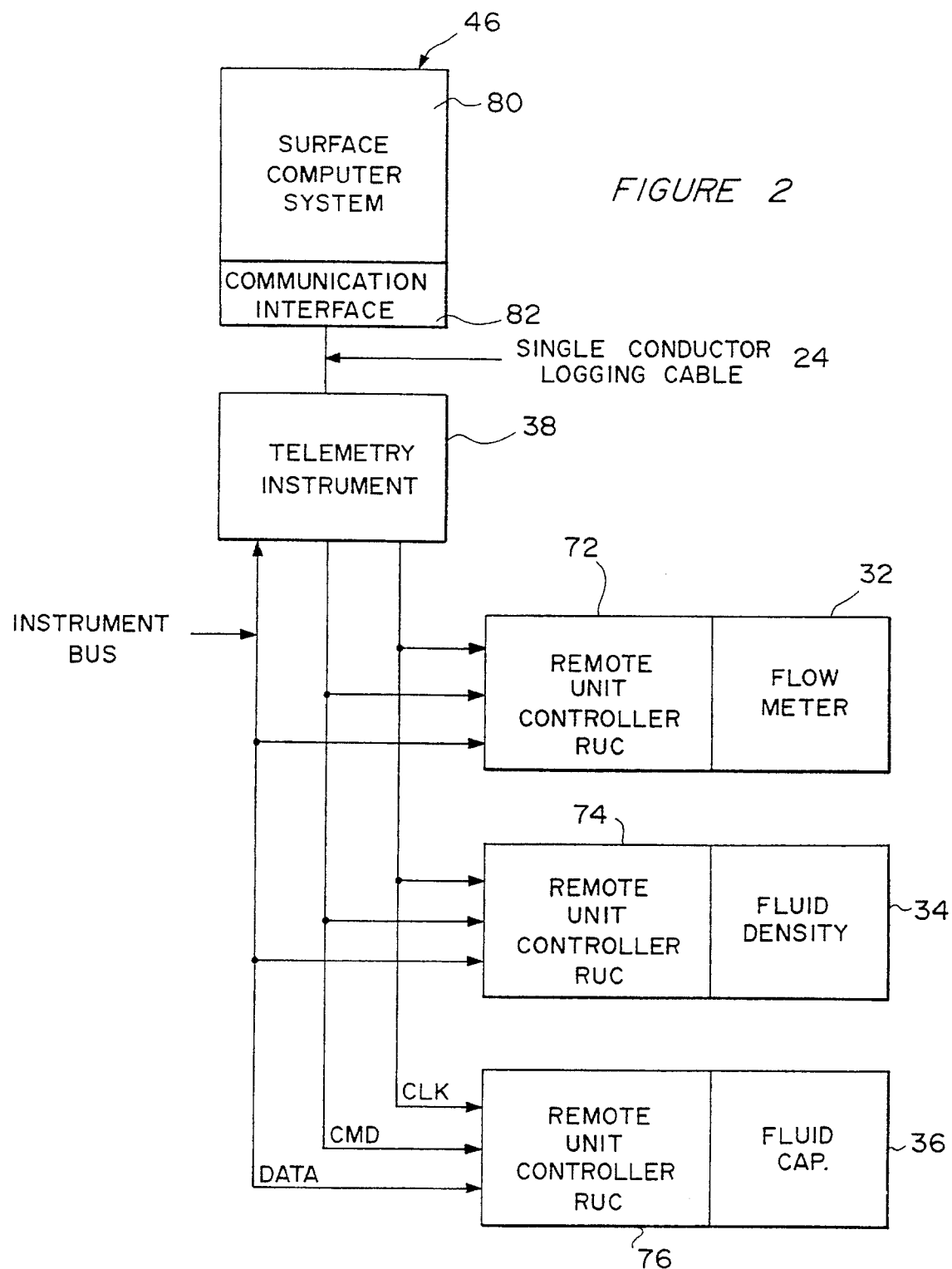
FIG. 2 is a block diagram schematic of the electronic circuitry for operating the logging instrument combination and transmitting the gathered data to surface electronics for determining the flow rates and total individual phase volumetric flow fractions of a multi-phase fluid flow.

Referring now to FIG. 2, a block diagram schematic of the data acquisition telemetry and data handling functions of the system are shown. Each instrument, flowmeter 32, fluid density instrument 34 and fluid capacitance instrument 36, are interconnected to respective remote unit controllers 72, 74 and 76 for controlling the operation of the instruments by commands from the surface computer system 80 operating through the communication interface unit 82, wireline cable 24, and through the downhole data acquisition and telemetry unit 38. Measured data from instruments 32, 34 and 36 may be sent via the instrument bus "data" line to the telemetry unit 38 and through the cable 24 to the surface computer system 80.

To generate response curves of the fluid density and fluid capacitance instruments, a surface test facility such as a flow loop may be utilized to simulate various downhole conditions and obtain the test response curve data. The test flow loop is a surface facility which directs a flow of desired rate and flow composition through a pipe of chosen inside diameter and deviation angle. The pipe is transparent, permitting visual assesment of the nature of the flow. Individual flows of water and oil may be withdrawn from storage tanks by a system of pumps. The pumps discharge their flows to a set of metering sections where the individual flow rates are controlled at selected values. After metering, the individual flows are combined and the combined flow passes through the transparent pipe. To generate the predicted response curves, a logging instrument combination is situated within the pipe, and the instrument responses are computer-recorded during passage of the flow.

The logging combination used in preparing the response curves includes a basket (diverting) flowmeter 22 at the bottom of the string. Situated above the flowmeter are fluid density 34 and fluid capacitance 36 instruments, with the fluid density instrument located just above the flowmeter. At the top of the logging combination is a data acquisition instrument 38 which allows simultaneous recording of flowmeter, fluid density, and fluid capacitance responses as hereinabove described.

An oil-water regime flow of known total flow rate and water cut is introduced at the bottom end of the transparent pipe. As the flow moves up the pipe. it passes through the basket flowmeter 32 where the flow of the mixture is measured and a signal sent to the telemetry unit 38. From the basket flowmeter, the flow is discharged to the fluid density and fluid capacitance instruments, 34 and 36, as described above. As the flow passes these instruments, their responses are simultaneously transmitted to a computer system where they are recorded. The response curves are generated by plotting data recorded from the fluid density and fluid capacitance tools during passage of various preselected oil-water flows through the transparent flow-loop pipe.

Figure 3:
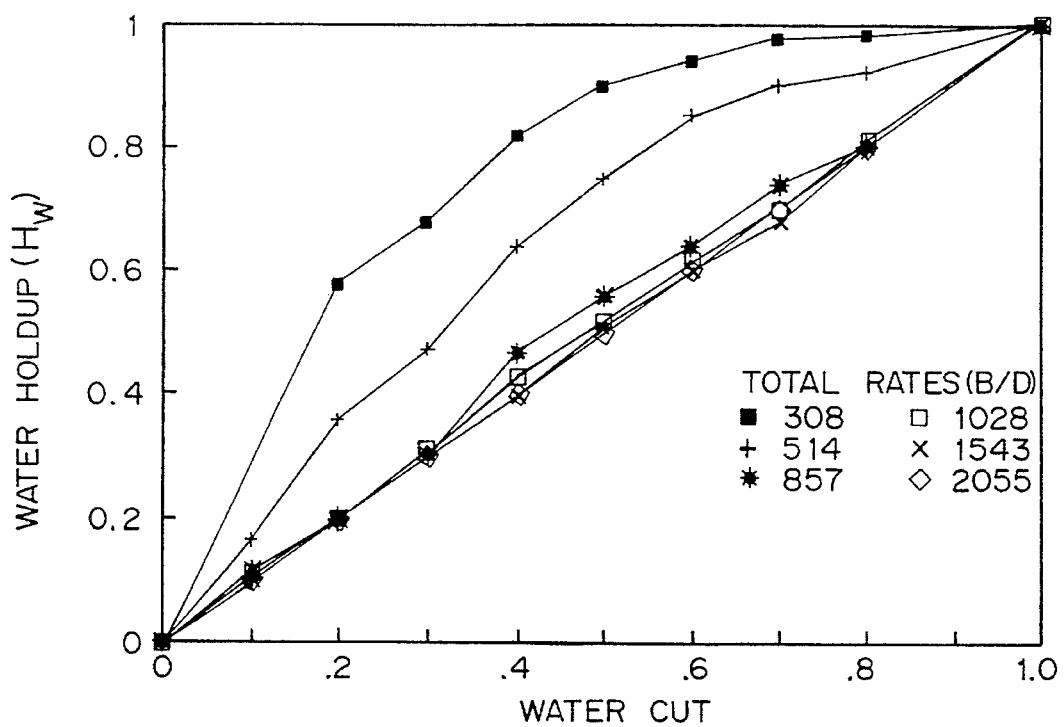
FIG. 3 is a graphical representation of predicted response curves for an oil-water fluid flow reflecting water cut plotted versus water hold up values determined in response to measurements obtained by the fluid density logging instrument in a test flow loop at selected total fluid flow rates.

FIG. 3 illustrates the response curves of the fluid density instrument 34 for oil-water flows in a 2.5-in. ID pipe at a 45° deviation angle. The vertical axis is the water holdup, Hw. The value of the holdup is determined from the measured density of the oil-water mixture ρm, and the densities of the individual oil and water phases, ρo and ρw:

$$Hw = \frac{\rho m - \rho o}{\rho w - \rho o} \quad (1)$$

The horizontal axis of the curve is the water cut, which is the ratio of the flow rate of water to the total flow rate of water and oil. The water cut value is established from the individual rates of the water and oil flows. Each response curve pertains to a constant total flow rate. For example, the curve for 308 B/D is obtained by plotting the water cut value (from the metering sections during flow loop data collection) versus the corresponding holdup value (from the measured fluid density during flow loop data collection) for water cuts of 0, 0.2, 0.4, 0.6, 0.8, and 1.0. At each of these water cuts, the total flow rate of water and oil, as controlled by the metering sections, is 308 B/D. To complete the response curve, the plotted points are joined by straight line segments. In addition to the curve for 308 B/D, other response curves are shown for 514, 857, 1028, 1543, and 2055 B/D.

All response curves pass through the point at 0 water cut, 0 Hw and the point at 1.0 water cut, 1.0 Hw. In addition, notice that the response curves for the higher flow rates are located close to a 45° line. Finally, note that for a given value of the water holdup, the value of the water cut increases with the corresponding value of the total flow rate.

Figure 4:
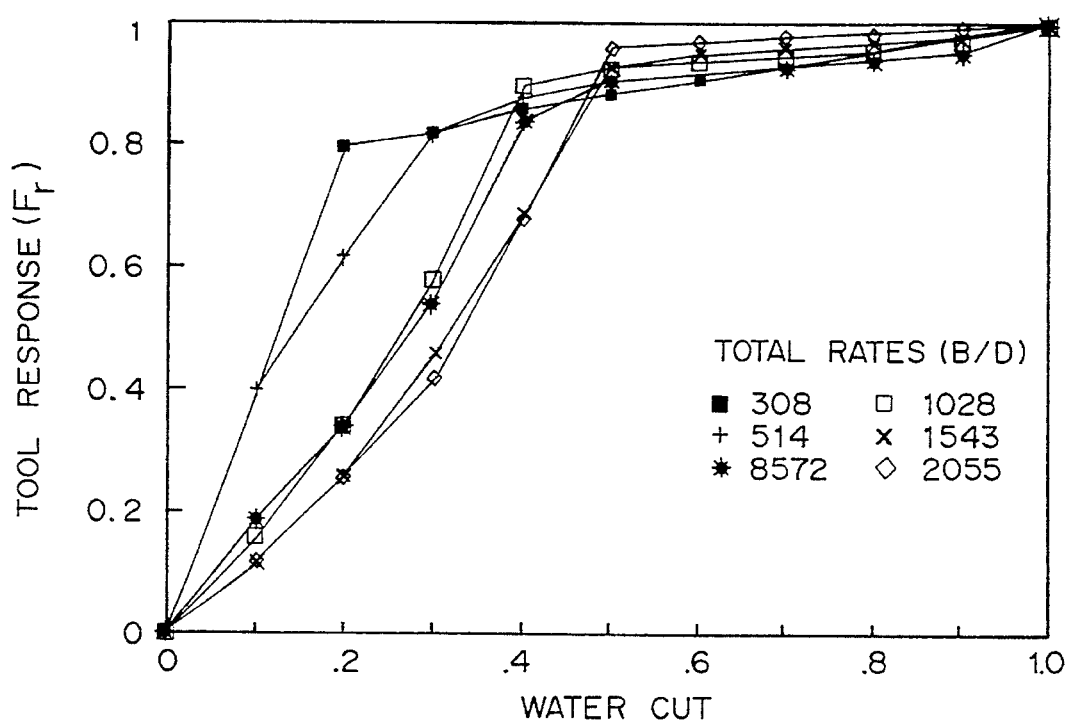
FIG. 4 is a graphical representation of predicted response curves for an oil-water fluid flow reflecting water cut plotted versus fractional tool response values determined in response to measurements obtained by the fluid capacitance logging instrument in a test flow-loop at a selected total fluid flow rate rates.

FIG. 4 illustrates the response curves of the fluid capacitance instrument 36 for oil-water flows in a 2.5-in. ID pipe at a 45° deviation angle. The vertical axis represents the fractional instrument response, Fr. This is determined from the frequency response of the instrument to an oil-water mixture, fw, the frequency response to water, fω, and the frequency response to oil, fo:

$$F_r = \frac{fm - fo}{fw - fo} \quad (2)$$

As before, the horizontal axis represents the water cut, which is determined from the individual water and oil flow rates.

Each response curve relates to a constant total flow rate. As an example, the curve for 308 B/D is derived by plotting the water cut value (from the metering sections during flow loop data collection) versus the corresponding value of the fractional instrument response (from the measured frequency of the fluid capacitance instrument during flow loop data collection) for water cuts of 0, 0.2, 0.4, 0.6, 0.8, and 1.0. At each of these cuts, the total flow rate of water and oil, as controlled by the metering sections, is 308 B/D. The response curve is completed by joining the plotted points with straight line segments. In addition to the curve for 308

B/D, response curves are shown for 514, 857, 1028, 1543, and 2055 B/D.

All response curves pass through the point at 0 water cut, 0 Fr, as well as the point at 1.0 water cut, 1.0 Fr. For a given value of the fractional instrument response, the water cut increases with the corresponding value of the total flow rate. An exception to this general behavior occurs in the upper right-hand portion of the plots, where the water cut decreases with increasing flow rate.

Figure 5:
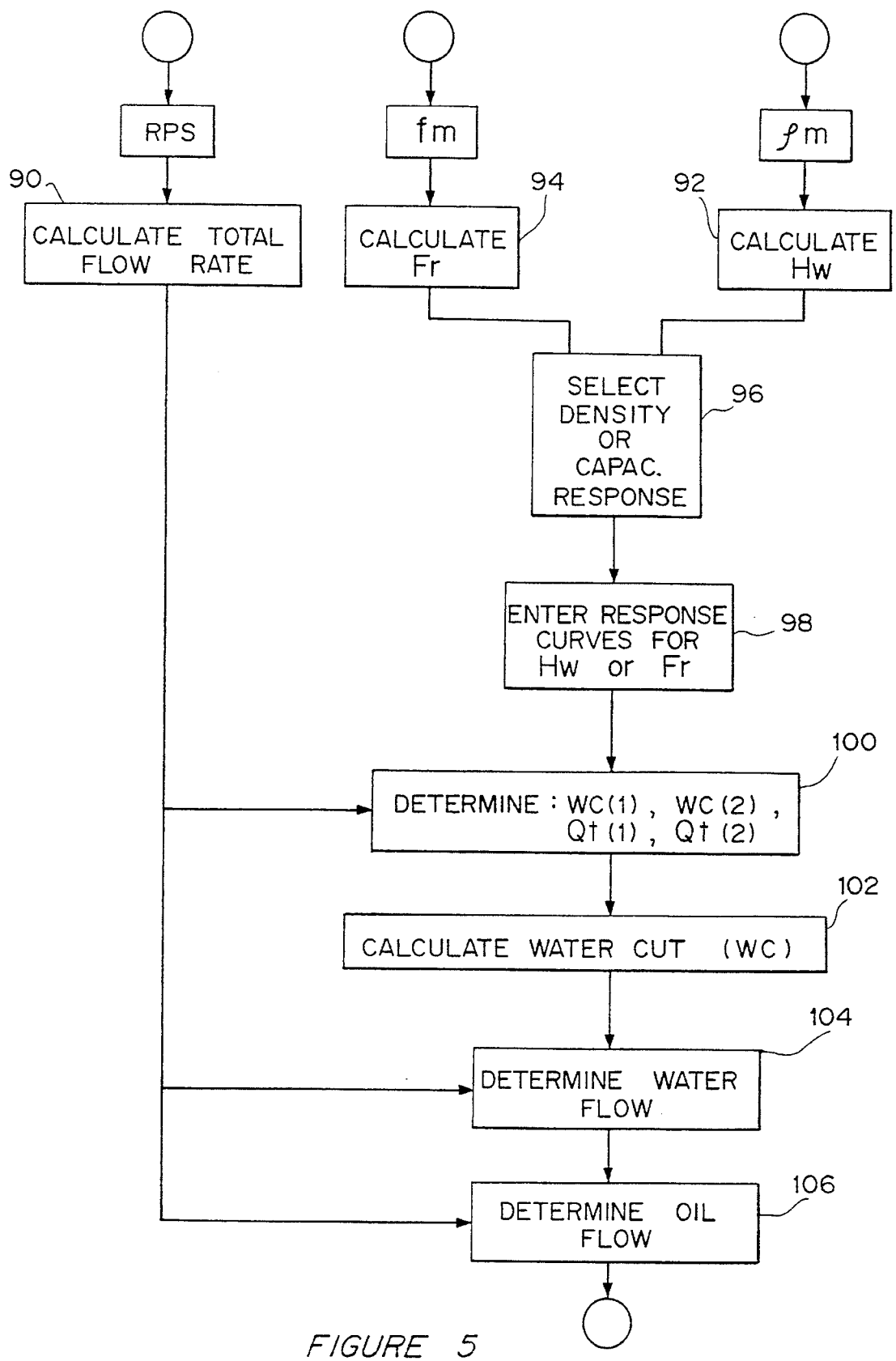
FIG. 5 is a flow chart diagram of the steps necessary to calculate water cut, the volumetric fractional flow of the water and the volumetric fractional flow of the oil in an oil-water regime.

FIG. 5 is a flow chart diagram of the necessary interpretative conversion and calculation steps to be performed by the surface computer system 80. The predicted response curves (see FIGS. 3 and 4) can be used to interpret actual downhole recorded measurements from the basket flowmeter, fluid density, and fluid capacitance instruments into the corresponding values of the total flow rate and the water cut. The first step 90 of the interpretation is to convert the revolutions per second (RPS) response of the flowmeter 32 to the total flow rate of oil and water. In a 2.5-in ID pipe, for example, the relationship of the RPS of the flowmeter to the total flow rate is highly linear over a wide range of total flow rates and water cuts. Consequently, the measured RPS can be divided by the sensitivity of the linear relationship (0.025 RPS/B/D) to obtain the total flow rate Qt). The accuracy of this technique is illustrated by Table I, which presents a set of actual total flow rates and water cuts in 2.5-in. ID pipe at a 45° deviation angle. Each line of the table shows an actual water cut and total flow rate, and in addition, the estimated value of the total flow rate obtained from dividing the RPS of the flowmeter by the sensitivity value just stated. The excellent agreement between the actual and estimated total flow rates demonstrates the linearity of the flowmeter in the 2.5-inch ID pipe.

TABLE I

Actual and estimated total flow rates at 45° deviation

| Water Cut | Total Flow Rate (Actual B/D) | Total Flow Rate (Estimated B/D) |
|---|---|---|
| 0.800 | 2055 | 2055 |
| 0.740 | 1542 | 1538 |
| 0.765 | 1492 | 1477 |
| 0.700 | 1028 | 1019 |
| 0.814 | 735 | 737 |
| 0.800 | 685 | 687 |
| 0.863 | 635 | 641 |
| 0.600 | 514 | 523 |
| 0.400 | 400 | 416 |
| 0.370 | 488 | 492 |
| 0.226 | 398 | 412 |

The next interpretative step 92 is to calculate water holdup Hw from the fluid density measurement provided by the fluid density instrument 34 in accordance with equation (1) hereinabove provided. Then the fractional response value Fr is calculated in step 94 in response to the fω frequency measurement provided by the fluid capacitance instrument 36. The fractional response Fr may be calculated using the equation (2) previously described. The next interpretive step 96 is to convert the value of Hw (or Fr), as obtained from the measured fluid density (or frequency of the fluid capacitance) instrument, to the corresponding value of the water cut. This is accomplished through a linear interpolation which is illustrated procedurally with respect to the fluid density response curves. In practice one may be selected or both may be utilized as a cross-check. At step 98, the specific value of Hw on the vertical axis of FIG. 3 is located and for this value of Hw, the response curves will provide values of water cut for the total flow rates of 308, 514, 857, 1028, 1543, and 2055 B/D. The next step 100 is to determine the response curve having the total flow rate closest to, but less than the flow rate from the first step 90. Denote the flow rate of this response curve as Qt (1). Denote the value of the water cut associated with this response curve value as WC(1).

Then note the response curve value for Hw having the total flow rate closest to but greater than, the flow rate from the first step 90. Denote the flow rate of this response curve as Qt (2). Denote the value of the water cut associated with the response curve value for Hw as WC(2). The next interpretative step 102 is to estimate the water cut in accordance with the following equation:

$$WC = WC(1) + \frac{(WC(2) - WC(1)) \times (Qt - Qt(1))}{Qt(2) - Qt(1)} \quad (3)$$

where: Qt is the total flow rate from the first step 90.

As hereinabove mentioned, the water cut (WC) can be calculated in the identical manner as just described using the density response curves by using the fluid capacitance response curves and proceeding through interpretative steps 96–102.

Once the water cut (WC) is known from step 102, the water volumetric flow (Qw) can be calculated in step 104 in accordance with the relationship:

$$Qw = WC \times Qt \quad (4)$$

Then in step 106, the oil volumetric flow (Qo) can be calculated in accordance with the relationship:

$$Qo = Qt - Qw \quad (5)$$

Once the flow values are known, the well production profile for the dual phase fluid regime is complete.

As stated earlier, either a fluid density or a fluid capacitance response can be used to estimate the water cut, provided that the total flow rate is already determined. The question arises as to which type of response is more desirable, and under what conditions. As a rule, a given type of response is less desirable when its response curve exhibits low sensitivity (change of response divided by change of water cut). Following this rule, the fluid capacitance response is least desirable at high water cuts combined with high total flow rates (see FIG. 4). By similar reasoning, the fluid density response is least desirable at high water cuts combined with low total flow rates (see FIG. 3). In most instances, however, experience shows that either response is applicable, although the fluid capacitance response is more definitive for a small change of total flow rate or water cut.

Several predictive tests have been run to check the interpretation accuracy of total flow rate and water cut under difficult circumstances. These tests consisted of a basket flowmeter response, a fluid density response, and a fluid capacitance response for conditions that generally do not coincide with a response curve. Each test was performed in a 2.5-in. ID at a 45 deviation angle, under the belief that such a test would be less difficult in a vertical pipe. Finally, four out of five of the following predictive tests pertain to high water cuts and most practitioners agree that high water cuts pose the most difficult conditions for accurate interpretations. In each predictive test the measured logging tool responses were analyzed to determine the total flow rate and the water cut, using the method previously described.

Predictive Test One: Major Water Contribution

Figure 6:
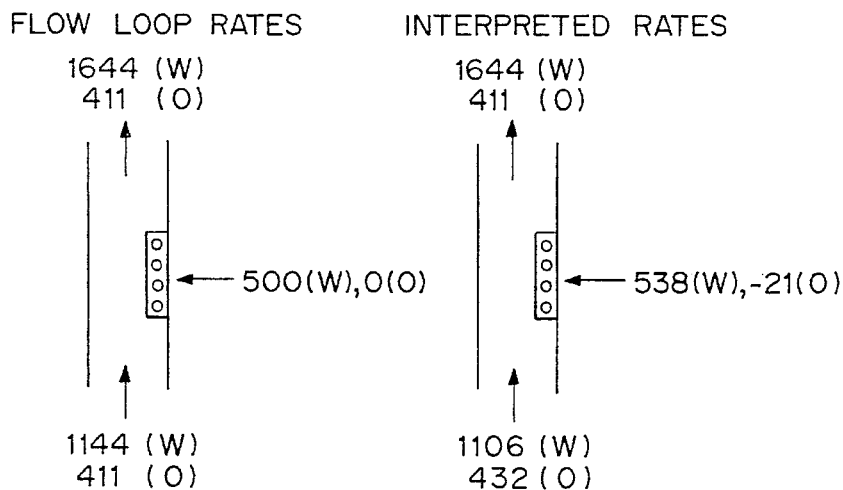
FIG. 6 is a simplified pictorial diagram illustrating one test situation involving a major water contribution to an oil-water flow regime.

Referring to FIG. 6, the left-hand diagram (labelled "Flow Loop rates") shows a flow of 1144 BWPD and 411 BOPD beneath an interval that contributes 500 BWPD and 0 BOPD. The resulting flow above the interval consists of 1644 BWPD and 411 BOPD.

A flow of 1644 BWPD together with 411 BOPD was established in the flow loop. The responses of the basket flowmeter, the fluid density and capacitance tools (hereafter, "the logging tools") were analyzed to determine the total flow rate and water cut which yielded the flow rates above the interval on the right-hand diagram in the flow loop, and the interpreted logging tool responses resulted in a total flow rate and water cut which yielded the flow rates shown below the interval. The water cuts were determined from the fluid density measurements. The contributions of the interval, found by subtracting the flow rates below the interval from the flow rates above the interval, are 538 BWPD and −21 BOPD (the minus sign indicates flow into, rather than out of, the interval).

This was a challenging test to find a major source of water by interpretation of the logging tool responses at high water cuts without misinterpreting some of the significant water contribution as an oil contribution. An example of such a misinterpretation would be 400 BWPD and 100 BOPD for the interval's contributions, as the 100 BOPD error would constitute a significant percentage of the 411 BOPD flow above and below the interval. Notice the high degree of accuracy of the interpreted contributions of the interval; an error of 38 BWPD at the level of 500 BWPD, and an error of 21 BOPD at the level of 411 BOPD.

Predictive Test Two: Major Water and Minor Oil Contributions

Figure 7:
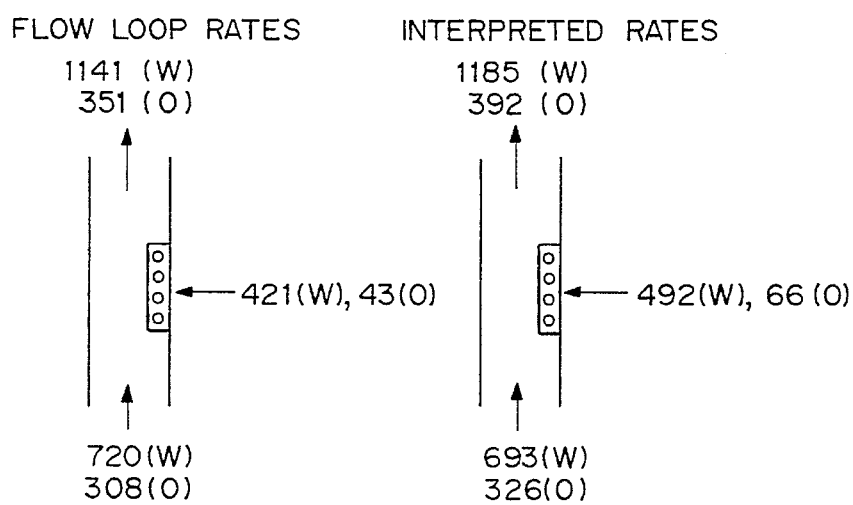
FIG. 7 is a simplified pictorial diagram illustrating a second test situation involving a major water and a minor oil contribution to an oil-water flow regime.

In FIG. 7, a high water cut flow of 720 BWPD and 308 BOPD combines with flow from an interval which contributes 421 BWPD and 43 BOPD, resulting in a flow above the interval of 1141 BWPD and 351 BOPD. These flows are shown by the left-hand diagram.

A flow of 1141 BWPD together with 351 BOPD was established in the flow loop and responses of the logging tools were recorded and interpreted as a total flow rate and water cut which yielded the flow rates above the interval in the right-hand diagram. Similarly, a flow of 720 BWPD together with 308 BOPD was established, and the interpreted logging tool responses yielded the flow rates below the interval in the right-hand diagram. The water cuts were determined from the fluid capacitance measurements. Subtraction of the flow rates below the interval from the flow rates above the interval resulted in the flow contributions according to the interpreted logging tool responses. The flow contributions, shown in the right-hand diagram, were 492 BWPD and 66 BOPD.

The interpreted logging tool responses successfully identified the major water contribution (492 interpreted vs 421 actual BWPD) and the much smaller oil contribution (66 interpreted vs. 43 actual BOPD. This example tested the capability of the logging tools to respond not only to the major water contribution, but also to the relatively small oil contribution, which was only one-tenth the magnitude of the water contribution.

Predictive Test Three: Minor Water Contribution

Figure 8:
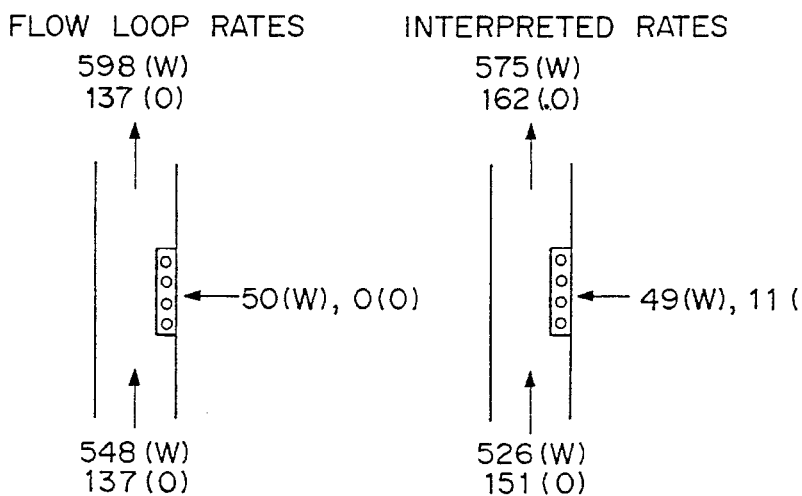
FIG. 8 is a simplified pictorial diagram illustrating a third test situation involving a minor water contribution to an oil-water flow regime.

In this case a highwater cut flow of 548 BWPD and 137 BOPD is joined by flow from an interval which contributes only 50 BWPD and no oil. These flows and the resultant flow above the interval are shown by the left-hand diagram in FIG. 8. The flows above and below the interval were established in the flow loop and the recorded logging tool responses were interpreted as total flow rates and water cuts which resulted in the flow rates shown by the right-hand diagram. The water cuts were determined from the fluid capacitance measurements. Subtraction of the flow rates beneath the interval from the flow rates above the interval yielded the contributions shown on the right-hand diagram, namely, 49 BWPD and 11 BOPD.

The combination of the logging tool responses and their interpretations successfully detected the small water contribution (49 interpreted vs. 50 actual BWPD) and the absence of oil production (11 interpreted vs. 0 actual BOPD). This example tested the ability of the logging tools to respond to, and measure, the increase of 50 B/D total flow rate. In addition, the example challenged the logging tools to distinguish the small increase as water, and not as oil.

Predictive Test Four: Minor Oil Contribution

Figure 9:
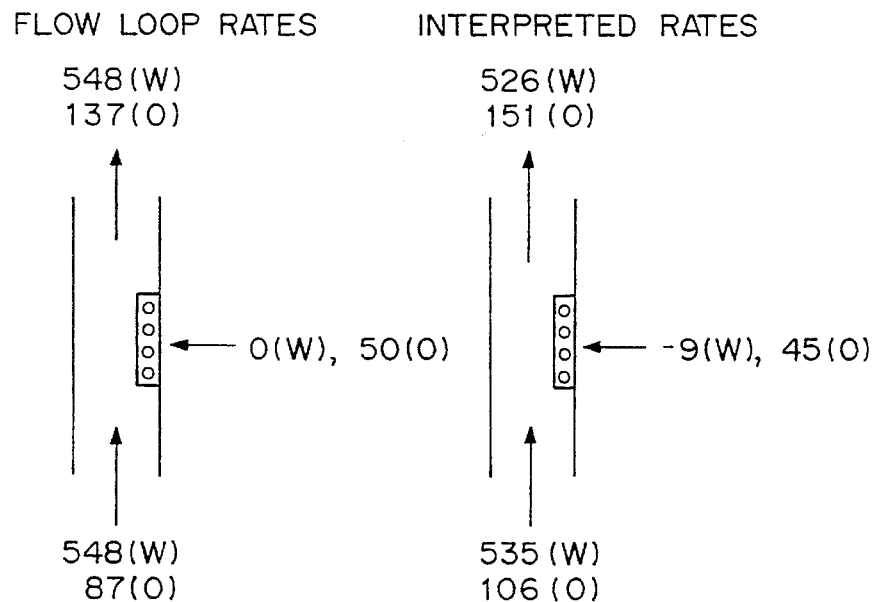
FIG. 9 is a simplified pictorial diagram illustrating a fourth test situation involving a minor oil contribution to an oil-water flow regime.

In this example (see left-hand diagram, FIG. 9) a high water cut flow of 548 BWPD and 87 BOPD combined with flow from an interval that contributed no water and only 50 BOPD. The combined flow is shown above the interval. The flows above and below the interval were established in the flow loop, and the combination of the logging tool responses and their interpretations resulted in total flow rates and water cuts which yielded the corresponding flow rates shown by the right-hand diagram. The water cuts were determined from the fluid capacitance measurements. According to the interpreted rates shown on this diagram, the interval accepts 9 BWPD and contributes 45 BOPD.

In this case, the interpreted logging tool responses correctly detected the small oil contribution (45 interpreted vs 50 actual BOPD) and the absence of water production (−9 interpreted vs 0 actual BWPD). This case tested the ability of the logging tools to respond to, and measure, the small increase of the total flow rate (50 B/D). The ability of othe logging tools to distinguish the increase as oil, not as water, was also tested.

Predictive Test Five: Water Contribution

Figure 10:
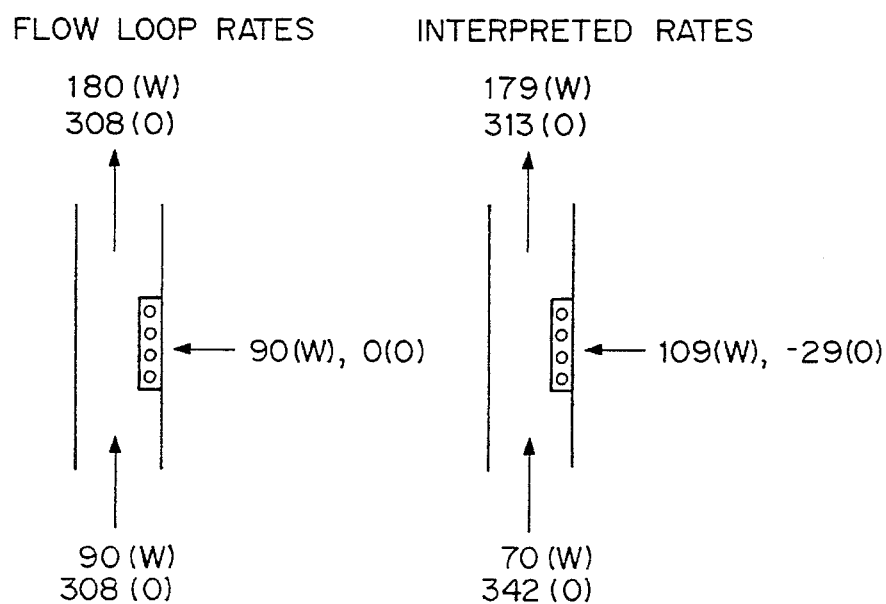
FIG. 10 is a simplified pictorial diagram illustrating a fifth test situation involving a major water contribution to an oil-water flow regime.

Referring to FIG. 10, the left-hand diagram shows a low water cut flow of 90 BWPD and 308 BOPD which combines with flow from an interval contributing 90 BWPD and no oil. The combined flow of 180 BWPD and 308 BOPD is shown above the interval.

The flows above and below the interval were established in the flow loop, and the interpreted logging tool responses yielded total flow rates and water cuts which resulted in the flow rates shown above and below the interval in the right-hand diagram. The water cuts were determined from the fluid density meassurements. According to the right-hand diagram, the interval contributes 109 BWPD and accepts 29 BOPD.

In this example, the interpreted logging tool response successfully detected the water contribution (109 interpreted vs. 90 actual BWPD). With respect to the oil contribution (−29 interpreted vs 0 actual BOPD), the error of 29 B/D is small relative to the flow rate of oil above and below the interval, namely, 308 BOPD.

As can be seen from the successful tests and using the interpretive method based on derived response curves, the measurements from a logging combination (comprised of a basket flowmeter, fluid density, and fluid capacitance tools) can be interpreted into reliable values of the total flow rate and the water cut in an oil-water flow. The reliability of the interpreted total flow rates and water cuts resulting from the method is confirmed by a set of flow loop tests in a 2.5-in. ID pipe at a 45 deviation angle. In oil-water flows under these test conditions, the method successfully detects both large and small changes of the total flow rate. For each change of the total flow rate, the method accurately determines how much is due to a change of the oil flow, and how much is due to a change of the water flow. With the logging tools and their interpretations' ability to detect a change of the total flow rate and apportion the change between the oil and water flows, this new method is ideal for profiling production in a well which produces both liquids.

The disclosed method and apparatus have been tested at various wellbore deviation angles with success. However, above a deviation angle of 75°–80° the accuracy of the fluid density and fluid capacitance instruments falls off because of the increasing inability of the instruments to accurately measure the multi-phase flow regime due the "near the center-line" of the borehole measuring geometry and the strata separation of the fluid phases.

Numerous variations and modifications may be made in the structure herein described without departing from the present invention. Accordingly, it should be clearly understood that the forms of the invention herein described and shown in the figures of the accompanying drawing are illustrative only and are not intended to limit the scope of the invention.

We claim:

1. A method of determining the flow rate of a selected single phase of a flow mixture having at least two phases expressed as fraction of the total flow rate of the flow mixture in a wellbore having a known deviation angle less than 90°, comprising the steps of:

generating a set of predicted response curves wherein each such response curve relates discrete selected values of the flow rate of the selected single phase of the flow mixture having at least two phases expressed as a fraction of the total flow rate of the flow mixture to test values representative of the volumetric concentration of the selected single phase of the flow mixture functionally related to measured responses of a selected logging instrument capable of distinguishing between the at least two phases of the flow mixture for a selected fluid mixture total flow rate and at a borehole deviation within a selected deviation range that includes the known borehole deviation;

measuring in the borehole the total flow rate of the fluid mixture including the selected single phase thereof;

measuring in the borehole values representative of said responses of said selected logging instrument distinguishing between the at least two phases of the flow mixture;

generating a value representative of the volumetric concentration of the selected single phase of the flow mixture functionally related to said measured value representative of said responses of said selected logging instrument; and determining from said set of predicted response curves an estimated value of the flow rate of the selected single phase of the flow mixture expressed as a fraction of the total flow rate of the flow mixture at said measured borehole total flow rate of the fluid mixture in response to said generated value representative of said volumetric concentration of the selected single phase of the flow mixture.

2. A method of determining the water cut of an oil-water flow in a wellbore having a known deviation angle less than 90°, comprising the steps of:

generating a set of predicted response curves wherein each such response curve relates discrete selected values of the water cut to test values representative of the volumetric concentration of the water phase of the flow mixture functionally related to measured responses of a selected logging instrument capable of distinguishing between the water and oil phases of the flow mixture for a selected oil-water total flow rate and at a borehole deviation within a selected deviation range that includes the known borehole deviation;

measuring in the borehole the total flow rate of the oil-water mixture;

measuring in the borehole values representative of said responses of said selected logging instrument distinguishing between the oil and water phases of the oil-water mixture;

generating a value representative of the volumetric concentration of the water phase of the oil-water mixture functionally related to said measured value representative of said responses of said selected logging instrument; and determining from said set of predicted response curves an estimated value of the water cut of the oil-water mixture at said measured borehole total flow rate of the oil-water mixture in response to said generated value representative of said volumetric concentration of the water phase of the flow mixture.

3. A method of profiling the multiple phases of a flow mixture having at least two phases in a wellbore having a known deviation angle less than 90°, comprising the steps of:

generating a set of predicted response curves wherein each such response curve relates discrete selected values of the flow rate of a selected single phase of the flow mixture having at least two phases expressed as a fraction of the total flow rate of the flow mixture to test values representative of the volumetric concentration of said selected single phase of the flow mixture functionally related to measured responses of a selected logging instrument capable of distinguishing between the at least two phases of the flow mixture for a selected fluid mixture total flow rate and at a borehole deviation within a selected deviation range that includes the known borehole deviation;

measuring in the borehole the total flow rate of the fluid mixture including said selected single phase thereof;

measuring in the borehole values representative of said responses of said selected logging instrument distinguishing between the at least two phases of the flow mixture;

generating a value representative of the volumetric concentration of said selected single phase of the flow mixture functionally related to said measured value representative of said responses of said selected logging instrument;

determining from said set of predicted response curves an estimated value of the flow rate of said selected single phase of the flow mixture expressed as a fraction of the total flow rate of the flow mixture at said measured borehole total flow rate of the fluid mixture in response to said generated value representative of said volumetric concentration of said selected single phase of the flow mixture;

determining the flow rate of said selected single phase of the flow mixture as a product of said measured total flow rate and said value of the flow rate of said selected single phase of the fluid mixture expressed as a fraction of the total flow rate; and determining the flow rate of said remaining phase of multiple phase fluid mixture functionally related to said determined flow rate of said selected single phase and said total flow rate of the mixture.

4. Apparatus for determining the flow rate of a selected single phase of a flow mixture having at least two phases expressed as fraction of the total flow rate of the flow mixture in a wellbore having a known deviation angle less than 90° comprising:

test flow loop means for generating a set of predicted response curves wherein each such response curve relates discrete selected values of the flow rate of the selected single phase of the flow mixture having at least two phases expressed as a fraction of the total flow rate of the flow mixture to test values representative of the volumetric concentration of the selected single phase of the flow mixture functionally related to measured responses of a selected logging instrument capable of distinguishing between the at least two phases of the flow mixture for a selected fluid mixture total flow rate and at a borehole deviation within a selected deviation range that includes the known borehole deviation:

flow measurement means for measuring in the borehole the total flow rate of the fluid mixture including the selected single phase thereof;

means disposed in the borehole for measuring values representative of said responses of said selected logging instrument distinguishing between the at least two phases of the flow mixture;

means for generating a value representative of a characteristic of the selected single phase of the flow mixture functionally related to said measured value representative of said responses of said selected logging instrument; and means for determining from said set of predicted response curves an estimated value of the flow rate of the selected single phase of the flow mixture expressed as a fraction of the total flow rate of the flow mixture at said measured borehole total flow rate of the fluid mixture in response to said generated value representataive of said volumetric concentration of the selected single phase of the flow mixture.

\* \* \* \* \*